(12) United States Patent
Tanaka et al.

(10) Patent No.: US 6,875,461 B2
(45) Date of Patent: Apr. 5, 2005

(54) METHOD FOR COATING OF BIOTISSUE SUBSTRATES

(75) Inventors: Junzo Tanaka, Tsukuba (JP); Hironobu Fukuzaki, Tatsuno (JP); Yoichi Oka, Tsukuba (JP); Isamu Yamaguchi, Tsukuba (JP)

(73) Assignees: Taki Chemical Co., Ltd., Hyogo (JP); National Institute for Materials Science, Ibaraki (JP)

( * ) Notice: Subject to any disclaimer, the term of this patent is extended or adjusted under 35 U.S.C. 154(b) by 0 days.

(21) Appl. No.: 10/474,646

(22) PCT Filed: Jun. 17, 2002

(86) PCT No.: PCT/JP02/05999

§ 371 (c)(1),
(2), (4) Date: Oct. 9, 2003

(87) PCT Pub. No.: WO03/000306

PCT Pub. Date: Jan. 3, 2003

(65) Prior Publication Data

US 2004/0109934 A1 Jun. 10, 2004

(30) Foreign Application Priority Data

Jun. 20, 2001 (JP) ........................................ 2001-185692

(51) Int. Cl.⁷ ............................ A61L 21/00; B05D 3/00
(52) U.S. Cl. ...................... 427/2.1; 427/2.24; 427/333; 427/430.1
(58) Field of Search ................................. 427/2.1, 2.24, 427/333, 419.1, 419.7, 430.1

(56) References Cited

U.S. PATENT DOCUMENTS 6,569,489 B1 * 5/2003 Li ............................. 427/2.26

FOREIGN PATENT DOCUMENTS

| EP | 0750587 | 1/2000 |
| JP | 04-059611 | 2/1992 |
| JP | 2000-327314 | 11/2000 |
| JP | 2001-137329 | 5/2001 |
| WO | WO01/36012 | 5/2001 |

OTHER PUBLICATIONS

International Search Report, PCT/JP02/05999, Aug. 15, 2002.

* cited by examiner

Primary Examiner—Brian K. Talbot
(74) Attorney, Agent, or Firm—Kolisch Hartwell, P.C.

(57) ABSTRACT

In a method for coating a calcium phosphate compound on a biotissue substrate or, particularly, in case the biotissue substrate is biotissue, there is provided a method for coating of biotissue substrate where the method causes no damage thereto, is very mild even to biotissues which are other than the biotissue to be coated and is able to form a uniform coat. A method for coating a calcium phosphate compound on a biotissue substrate by an alternate soaking method which is characterized in that, as the soaking solutions, there are used a solution containing a water-soluble calcium salt and borate and/or L-histidine and a phosphate solution.

7 Claims, No Drawings

METHOD FOR COATING OF BIOTISSUE SUBSTRATES

TECHNICAL FIELD

An object of the present invention is that, in a method for coating a calcium phosphate compound on a biotissue substrate or, particularly, in case the biotissue substrate is biotissue, there is provided a method for coating of biotissue substrate where the method causes no damage thereto, is very mild even to biotissues which are other than the biotissue to be coated and is able to form a uniform coat.

BACKGROUND OF THE INVENTION

In the reconstruction of damaged ligament in orthopedics, a method where autologous tendon is passed through a bone tunnel opened in bone and fixed thereto has been widely used.

In such a method, adhesion of tendon which is a soft tissue to bone which is a hard tissue is essentially bad and, therefore, adhesion and fixation of the transplanted tendon to the bone tunnel are bad and that is a cause which greatly affects the initiation of rehabilitation after the operation and retards its recovery.

For improvement of adhesion of biotissue to bone as such, there has been known a method in which biotissue, medical material, etc. are soaked in a calcium solution and a phosphate solution alternately so that a calcium phosphate compound is coated on the surface of the material to enhance the adhesion of biomaterial to bone (Japanese Patent Laid-Open 2000/327,314).

Further, the present inventors developed a method for fixing a calcium phosphate compound on the surface of tissue substrate for tendon or ligament which is biotissue in accordance with the above method and filed an application (Japanese Patent Application 11/323,753).

Such a method is a method which comprises a step where tissue substrate for tendon or ligament is alternately soaked in a calcium solution containing calcium ion but containing substantially no phosphate ion and a phosphate solution containing phosphate ion but containing substantially no calcium ion so that a calcium phosphate compound is formed and fixed at least on the surface of the substrate.

According to such a method however, when the biotissue substrate is alternately soaked in the above-mentioned solutions, pH of the solutions lowers as a result of formation of a calcium phosphate compound and there is a problem that, when a calcium phosphate compound is directly coated on the biotissue substrate, damage of the biotissue substrate is resulted.

Further, with regard to the osmotic pressure of such solutions, a solution having an osmotic pressure which is near that of body fluids is to be used and, when only a compound having a buffer effect which is commonly used is used, there is a limitation for its use because of the relation between the buffer effect and the osmotic pressure. Thus, it is the current status that a method for coating a calcium phosphate compound satisfying all of the requirements and having high safety to living body has not been found yet.

In view of the current status as mentioned above, the present inventors have repeatedly carried out intensive investigations for a method of coating the biotissue substrate where a calcium phosphate compound is coated on the biotissue substrate in which it is possible to form a uniform coat mainly comprising hydroxyapatite causing no damage of tissue to the biotissue substrate and, moreover, a soaking solutions satisfying the condition in relation to the osmotic pressure of body fluids are used.

DISCLOSURE OF THE INVENTION

It has been found as a result that, when a borate or L-histidine is used together with a water-soluble calcium salt as a soaking solution as such, the above-mentioned problem can be solved and, on the basis of such a finding, the present invention has been achieved.

Thus, the present invention relates to a method for coating a calcium phosphate compound on a biotissue substrate by an alternate soaking method which is characterized in that, as the soaking solutions, there are used a solution containing a water-soluble calcium salt and borate and/or L-histidine and a phosphate solution.

BEST MODE FOR CARRYING OUT THE INVENTION

The method for coating the biotissue substrate according to the present invention will be illustrated in more detail as hereunder.

The method for coating the biotissue substrate according to the present invention is a method where the biotissue is alternately soaked in a solution containing a water-soluble calcium salt and borate and/or L-histidine and a phosphate solution, whereby a calcium phosphate compound is coated on the biotissue substrate.

With regard to the solutions for soaking as such, there is exemplified a phosphate having a pH-buffering effect in the above Japanese Patent Laid-Open 2000/327,314 and a Tris buffer solution of calcium chloride, a Tris buffer solution of calcium acetate, etc. are exemplified.

However, they are only a part of exemplifications of a calcium compound and, with regard to the influence of the soaking solutions used in the present invention on the biotissue substrate, there is no consideration at all.

Incidentally, in a method for coating the biotissue substrate according to the present invention, the calcium phosphate which is a coating material is a calcium phosphate compound prepared by the chemical reaction of phosphoric acid with calcium and its examples are hydroxyapatite, tricalcium phosphate and octacalcium phosphate. Among them, it is most preferred to form hydroxyapatite from a viewpoint of its highest similarity to living body.

Firstly, with respect to a solution containing a water-soluble calcium salt and borate and/or L-histidine used in the present invention, examples of the water-soluble calcium salt used in the present invention are calcium chloride, calcium bromide, calcium iodide, calcium nitrate, calcium formate, calcium acetate, calcium propionate, calcium butyrate and calcium lactate and, in view of safety, solubility, cost, etc., the use of calcium chloride, calcium nitrate, calcium acetate and calcium lactate is preferred.

With regard to the borate, it is possible to use boric acid, sodium borate, potassium borate, ammonium borate, magnesium borate, lithium borate, etc. and the use of boric acid, sodium borate and potassium borate is preferred in view of safety, solubility, cost, etc.

In the water-soluble calcium salt solution containing borate and/or L-histidine as such, there is no particular limitation for the concentration of calcium ion in the solution but, when the produced amount of the calcium phosphate compound being produced by the reaction with a phosphate solution which will be mentioned later and, further, osmotic pressure of the solution are taken into consideration, 50 to 300 mmol/L is preferred.

With regard to the concentration of the borate and L-histidine in the water-soluble calcium salt solution, both of them are preferred to be 10 to 50 mmol/L.

Further, with regard to the pH of the calcium salt solution, it is desirable that the pH of the solution is preferably 6.5 to 8.0 and, particularly preferably, 7 to 7.6. Incidentally, pH of the solution may be adjusted by hydrochloric acid, sodium hydroxide, etc. if necessary and, at that time, it is necessary to use by taking the above-mentioned osmotic pressure of the solution into consideration.

Then, with regard to the phosphate solution used in the present invention, examples of the phosphate used in the present invention are phosphoric acid, disodium hydrogen phosphate, sodium dihydrogen phosphate, dipotassium hydrogen phosphate and potassium dihydrogen phosphate and, among those phosphates, joint use of disodium hydrogen phosphate and sodium dihydrogen phosphate is most preferred. With regard to the concentration of the phosphate in that case, it is preferred that disodium hydrogen phosphate is 10 to 200 mmol/L and sodium dihydrogen phosphate is 5 to 150 mmol/L by taking the pH-buffering effect, the osmotic pressure of the solution and the condition where hydroxyapatite is apt to be produced as the calcium phosphate compound into consideration.

Further, with regard to the pH of such a phosphate solution, it is desirable that the pH is 6.5 to 8.0 or, particularly preferably, the pH is 7.0 to 7.6. Incidentally, pH of the solution may be adjusted by hydrochloric acid, sodium hydroxide, etc. if necessary and, at that time, it is necessary to use by taking the above-mentioned osmotic pressure of the solution into consideration.

Osmotic pressures of the above calcium salt solution and phosphate solution are dependent upon the concentrations of the added salts and, although there is no particular limitation therefor, it is necessary to make it as same as osmotic pressure of a physiological saline solution when its influence on living body is taken into consideration. To be more specific, it is preferably 200 to 400 mmol/kg or, more preferably, 250 to 350 mmol/kg.

With regard to the order of soaking of the biotissue into those solutions, any of the orders where the solution containing the water-soluble calcium salt and borate and/or L-histidine is firstly used and the solution containing the phosphate is firstly used is acceptable.

Anyway, it is sufficient that the above-mentioned calcium salt solution and phosphate solution are alternately used for the soaking. Incidentally, it is desirable in that case that, after the biotissue substrate is soaked in any of the solutions, washing is conducted using a physiological saline solution or the like as a solution containing substantially no calcium ion and phosphate ion.

As a result of the washing as such, excessive calcium ion or phosphate ion adhered on the surface of the biotissue substrate can be removed whereby an excessive formation of a calcium phosphate compound can be prevented.

With regard to temperature of each of the solutions in conducting the soaking, there is no particular limitation for its range although, in the case of coating together with excising the biotissue substrate from living body, it is desirable to conduct preferably at 0 to 50° C. or, more preferably, 20 to 40° C.

With regard to the biotissue substrate on which a calcium phosphate compound is coated by such an alternate soaking method, there is no particular limitation for its type but tendon, ligament, etc. may be exemplified and, in surgical treatment, it is possible to directly coat on the biotissue substrates. It is also possible to coat using tendon, ligament, etc. excised by a surgical means from living body such as animal and, in any case, as to a biotissue substrate to which such a coating is carried out, the use of autologous tissue is particularly preferred.

Further, the coating method according to the present invention is also able to be applied to biomaterial except biotissue substrate and examples of such biomaterial are chitin, chitosan, sodium alginate, collagen, gelatin, mucopolysaccharide, polylactic acid, polyglycolic acid, polyurethane, polyethylene, polypropylene, polyester, Nylon, polycarbonate, Teflon, silicone, poly-y-glutamic acid and cellulose.

EXAMPLES

Now the present invention will be further illustrated by way of the following Examples although the present invention is not limited thereto. Incidentally, % in the Examples is that by weight in all cases unless otherwise mentioned.

Example 1

Five grams of chitosan (Pure Chitosan manufactured by K. K. Kyowa Technos) having a number-average molecular weight of 270,000 and a deacetylation degree of 90% were dissolved in 95 g of 1% aqueous solution of acetic acid, poured into a Teflon tube having an inner diameter of 3 mm and frozen at −80° C. to freeze-dry. The resulting dried chitosan was taken out from the tube and cut into a size of 40 mm length.

This was soaked in 1 mol/L sodium hydroxide for 2 hours and well washed with distilled water to give a chitosan stick.

The resulting chitosan stick was soaked for 30 minutes at 37° C. under a gentle stirring in 20 ml of a calcium salt solution containing 100 mmol/L of calcium chloride (reagent of a special grade manufactured by Wako Pure Chemical) and 30 mmol/L of L-histidine (reagent of a special grade manufactured by Wako Pure Chemical). Then it was washed with 20 ml of a physiological saline solution for 30 seconds and soaked for 30 minutes at 37° C. under a gentle stirring in 20 ml of a phosphate solution containing 25 mmol/L of sodium dihydrogen phosphate (reagent of a special grade manufactured by Wako Pure Chemical) and 109 mmol/L of disodium hydrogen phosphate (reagent of a special grade manufactured by Wako Pure Chemical). After that, it was washed with 20 ml of a physiological saline solution for 30 seconds again.

The above-mentioned steps comprise one cycle and, in each of the steps, pH of the solution was measured and the solution was exchanged to a fresh one. Steps of five cycles in total were repeatedly carried out.

Osmotic pressures of the soaking solutions to be used were measured using a Vapro™ vapor-pressure osmometer 5520 type manufactured by Wescori.

Further, the adhered amount of the calcium phosphate compound after coating was measured by the following method. Firstly, the chitosan stick on which the calcium phosphate compound prepared by the above method was coated was well washed with distilled water, dried in vacuo and calcinated at 800° C. for 2 hours using an electric furnace. The inorganic substance remaining after the calcinating was regarded as calcium phosphate compound and the content of the inorganic substance was calculated from the change in the weight from the chitosan stick before calcinating and was used as the adhered amount of the calcium phosphate compound after the coating.

The result is shown in Table 1.

Example 2

The same operation as in Example 1 was carried out except that, in the calcium salt solution, concentration of calcium chloride was made 100 mmol/L and that of borax (reagent grade manufactured by Wako Pure Chemical) was made 10 mmol/L and pH was adjusted to 7.49 by 3.65% hydrochloric acid whereupon a coating treatment of chitosan stick was conducted. Result of the measurement is shown in Table 1 as well.

Example 3

The same operation as in Example 1 was carried out except that, in the calcium salt solution, concentration of calcium chloride was made 100 mmol/L and that of L-histidine was made 50 mmol/L whereupon a coating treatment of chitosan stick was conducted. Result of the measurement is shown in Table 1 as well.

Example 4

The same operation as in Example 1 was carried out except that, in the phosphate solution, concentration of sodium dihydrogen phosphate was made 30 mmol/L and pH was adjusted to 7.4 with sodium hydroxide whereupon a coating treatment of chitosan stick was conducted. Result of the measurement is shown in Table 1 as well.

Example 5

The same operation as in Example 1 was carried out except that, in the calcium salt solution, concentration of calcium nitrate (reagent of a special grade manufactured by Wako Pure Chemical) was made 100 mmol/L and that of L-histidine was made 30 mmol/L whereupon a coating treatment of chitosan stick was conducted. Result of the measurement is shown in Table 1 as well.

Example 6

The same operation as in Example 1 was carried out except that free tendon was surgically excised from a hind leg of slaughtered Japanese white rabbit and used it in place of the chitosan stick whereupon a coating treatment of free tendon was conducted. Result of the measurement is shown in Table 1 as well.

Comparative Example 1

The same operation as in Example 1 was carried out except that, in the calcium salt solution, concentration of calcium lactate (reagent of a special grade manufactured by Wako Pure Chemical) was made 145 mmol/L whereupon a coating treatment of chitosan stick was conducted. Result of the measurement is shown in Table 1 as well.

Comparative Example 2

The same operation as in Example 1 was carried out except that, in the calcium salt solution, concentration of calcium chloride was made 100 mmol/L and that of calcium nitrate was made 100 mmol/L whereupon a coating treatment of chitosan stick was conducted. Result of the measurement is shown in Table 1 as well.

Comparative Example 3

The same operation as in Comparative Example 1 was carried out except that a part of the free tendon surgically excised from hind leg of Japanese white rabbit excised in Example 6 was used whereupon a coating treatment of the free tendon was conducted. Result of the measurement is shown in Table 1 as well.

TABLE 1

|  | Ex 1 | Ex 2 | Ex 3 | Ex 4 | Ex 5 | Ex 6 | CE 1 | CE 2 | CE 3 |
|---|---|---|---|---|---|---|---|---|---|
| Calcium salt solution (Ca) | | | | | | | | | |
| pH | 7.68 | 7.49 | 7.51 | 7.68 | 7.50 | 7.68 | 7.11 | 7.70 | 7.11 |
| O. P.[*1] (mmol/kg) | 280 | 329 | 361 | 280 | 276 | 280 | 510 | 510 | 510 |
| Phosphate solution (P) | | | | | | | | | |
| pH | 7.41 | 7.41 | 7.41 | 7.41 | 7.41 | 7.41 | 7.41 | 7.41 | 7.41 |
| O. P.[*1] (mmol/kg) | 290 | 290 | 290 | 72 | 290 | 290 | 290 | 290 | 290 |
| Cycle | | | | | pH | | | | |
| 1 Ca | 7.69 | 7.54 | 7.66 | 7.55 | 7.61 | 7.68 | 7.10 | 7.76 | 7.13 |
| P | 7.32 | 7.45 | 7.48 | 7.43 | 7.38 | 7.36 | 7.53 | 7.52 | 7.47 |
| 2 Ca | 7.38 | 7.35 | 7.51 | 7.48 | 7.55 | 7.65 | 6.37 | 6.64 | 6.90 |
| P | 7.40 | 7.38 | 7.39 | 7.29 | 7.40 | 7.41 | 7.48 | 7.48 | 7.36 |
| 3 Ca | 7.15 | 7.31 | 7.52 | 7.25 | 7.36 | 7.60 | 6.18 | 6.55 | 6.81 |
| P | 7.31 | 7.34 | 7.34 | 7.13 | 7.36 | 7.36 | 7.47 | 7.47 | 7.40 |
| 4 Ca | 7.38 | 7.23 | 7.53 | 7.25 | 7.25 | 7.57 | 6.09 | 6.48 | 6.61 |
| P | 7.44 | 7.34 | 7.39 | 6.90 | 7.41 | 7.30 | 7.47 | 7.47 | 7.47 |
| 5 Ca | 7.37 | 7.07 | 7.50 | 7.30 | 7.28 | 7.41 | 6.08 | 6.35 | 6.58 |
| P | 7.33 | 7.33 | 7.30 | 6.80 | 7.35 | 7.35 | 7.48 | 7.48 | 7.30 |
| Inorg. Substance[*2] (%) | 32.8 | 34.4 | 28.4 | 9.3 | 33.6 | 8.90 | 26.9 | 33.6 | 8.05 |

Ex: Example
CE: Comparative Example
[*1]Osmotic Pressure
[*2]Content of Inorganic Substance When tissues of the surface layers of the free tendons subjected to a coating treatment in Example 6 and Comparative Example 3 were cut out and subjected to a cell culture test in vitro, the surface tissues of the tendon coated by the method of Example 6 according to the present invention showed a smooth growth while, in the surface tissues of the tendon coated by a method of Comparative Example 3, no growth was observed.

In addition, as will be apparent from the result of Table 1, in the coating method of the present invention, variation of pH of the soaking solution was small and the osmotic pressure was within a range of causing no affection on the biotissue. Accordingly, no influence on biotissue is resulted according to the method of the present invention.

INDUSTRIAL APPLICABILITY

In the method for coating of biotissue substrate according to the present invention, it is possible in a method for coating of a calcium phosphate compound on biotissue substrate that no damage of the tissue is resulted in the biotissue substrate and a coat mainly comprising uniform hydroxyapatite is formed. Moreover, it is a soaking solution satisfying the requirement in terms of a relation between body fluids and osmotic pressure and, therefore, its influence on biotissue is small.

Consequently, the coating method according to the present invention is particularly useful in such a case that a calcium phosphate compound is directly coated on biotissue substrate such as tendon or ligament which is biotissue.

What is claimed is:

1. A method for coating a calcium phosphate compound on a biotissue substrate, wherein a calcium salt solution and a phosphate solution are used as soaking solutions and the biotissue substrate is soaked in the calcium salt solution and the phosphate solution alternately, whereby the calcium phosphate compound is coated on the biotissue substrate, characterized in that, the calcium salt solution contains 50 to 300 mmol/L of a water-soluble calcium salt, 10 to 50 mmol/L of a borate and/or 10 to 50 mmol/L of L-histidine, and that the concentration of phosphate in the phosphate solution is 5 to 200 mmol/L.

2. The method of claim 1, wherein the water-soluble calcium salt is selected from calcium chloride, calcium nitrate, calcium acetate and calcium lactate.

3. The method of claim 1, wherein the borate is selected from boric acid, sodium borate and potassium borate.

4. The method of claim 1, wherein the phosphate solution includes disodium hydrogen phosphate and sodium dihydrogen phosphate.

5. The method of claim 4, wherein the concentration of disodium hydrogen phosphate is 10 to 200 mmol/L and the concentration of sodium dihydrogen phosphate is 5 to 150 mmol/L.

6. The method of claim 1, wherein the method uses a solution containing the water-soluble calcium salt and borate that has a pH of 6.5 to 8.0.

7. The method of claim 1, wherein the phosphate solution has a pH of 6.5 to 8.0.

* * * * *